US010004435B2

(12) United States Patent
Larvenz et al.

(10) Patent No.: US 10,004,435 B2
(45) Date of Patent: Jun. 26, 2018

(54) DEVICES AND METHODS FOR CONTINUOUS ANALYTE MONITORING

(71) Applicant: DexCom, Inc., San Diego, CA (US)

(72) Inventors: Shawn Larvenz, Ramona, CA (US); Katherine Yerre Koehler, San Diego, CA (US); Apurv Ullas Kamath, San Diego, CA (US); Rian Draeger, Portola Valley, CA (US); Subrai G. Pai, Atlanta, GA (US)

(73) Assignee: DexCom, Inc., San Diego, CA (US)

( * ) Notice: Subject to any disclaimer, the term of this patent is extended or adjusted under 35 U.S.C. 154(b) by 335 days.

(21) Appl. No.: 14/538,701

(22) Filed: Nov. 11, 2014

(65) Prior Publication Data

US 2015/0164390 A1 Jun. 18, 2015

Related U.S. Application Data

(60) Provisional application No. 61/904,341, filed on Nov. 14, 2013.

(51) Int. Cl.
*A61B 5/145* (2006.01)
*A61B 5/00* (2006.01)
*G16H 40/63* (2018.01)
*G06F 19/00* (2018.01)
*G16H 50/20* (2018.01)

(52) U.S. Cl.
CPC ........ *A61B 5/14532* (2013.01); *A61B 5/0004* (2013.01); *A61B 5/0022* (2013.01); *A61B 5/6824* (2013.01); *A61B 5/6831* (2013.01); *A61B 5/6898* (2013.01); *A61B 5/743* (2013.01); *A61B 5/7445* (2013.01); *A61B 5/7455* (2013.01); *A61B 5/7475* (2013.01);
(Continued)

(58) Field of Classification Search
CPC . A61B 5/0004; A61B 5/0022; A61B 5/14532; A61B 5/6824; A61B 5/6831; A61B 5/6898; A61B 5/743; A61B 5/7445; A61B 5/7455; A61B 5/7475; G06F 19/3406; G06F 19/345; G06F 19/3456
USPC ................. 600/345, 347, 365, 309
See application file for complete search history.

(56) References Cited

U.S. PATENT DOCUMENTS 8,309,357 B2 * 11/2012 Chang ................ A61B 5/14532
422/50
8,395,581 B2 * 3/2013 Graskov ............. G06F 19/3406
345/156
(Continued)

FOREIGN PATENT DOCUMENTS

WO WO 2013-090731 6/2013

*Primary Examiner* — Navin Natnithithadha
(74) *Attorney, Agent, or Firm* — Knobbe Martens Olson & Bear, LLP

(57) ABSTRACT

"Zero-click" viewing of sensor data without any user input is provided. A display with sensor data may be "always on," and may enable discrete viewing of sensor data without significant user hassle. Also, a system may be configured to display only current data, and/or to display the most current data for only a set interval. Also, one device in a continuous analyte monitoring system may be designated as a primary device, or hub, for receiving sensor data, and may control the flow of information and/or alerts to other devices in the system. Sensor data and/or alerts may be sent to a hierarchy of devices and/or persons in a designated order.

13 Claims, 7 Drawing Sheets

(52) U.S. Cl.
CPC ......... *G16H 40/63* (2018.01); *G06F 19/3456* (2013.01); *G16H 50/20* (2018.01); *Y02A 90/26* (2018.01)

(56) References Cited

U.S. PATENT DOCUMENTS

| | | | | |
|---|---|---|---|---|
| 8,506,524 B2* | 8/2013 | Graskov | ............. | A61M 5/1723 345/156 |
| 8,514,086 B2* | 8/2013 | Harper | ............... | A61B 5/14532 340/505 |
| 8,617,071 B2* | 12/2013 | Say | .................... | A61M 5/1723 422/50 |
| 8,816,862 B2* | 8/2014 | Harper | ............... | A61B 5/14532 340/505 |
| 8,920,332 B2* | 12/2014 | Hong | ................. | A61B 5/02427 600/309 |
| 9,011,331 B2* | 4/2015 | Say | .................... | A61M 5/1723 600/309 |
| 9,066,694 B2* | 6/2015 | Say | .................... | A61M 5/1723 |
| 9,119,528 B2* | 9/2015 | Cobelli | ................ | A61B 5/746 |
| 9,119,529 B2* | 9/2015 | Hampapuram | ........ | A61B 5/746 |
| 9,186,113 B2* | 11/2015 | Harper | ............... | A61B 5/14532 |
| 9,226,714 B2* | 1/2016 | Harper | ............... | A61B 5/14532 |
| 9,549,694 B2* | 1/2017 | Harper | ............... | A61B 5/14532 |
| 9,686,748 B2* | 6/2017 | Kim | .................... | H04W 52/027 |
| 2003/0208113 A1 | 11/2003 | Mault et al. | | |
| 2005/0182306 A1* | 8/2005 | Sloan | .................. | A61B 5/0002 600/300 |
| 2008/0287922 A1* | 11/2008 | Panduro | .............. | G06F 19/3456 604/890.1 |
| 2008/0300572 A1* | 12/2008 | Rankers | ............. | A61B 5/14532 604/504 |
| 2009/0018495 A1* | 1/2009 | Panduro | .............. | G06F 19/3468 604/67 |
| 2009/0212966 A1* | 8/2009 | Panduro | .............. | G06F 19/3468 340/4.31 |
| 2009/0326445 A1* | 12/2009 | Graskov | ............. | A61M 5/1723 604/67 |
| 2010/0010330 A1* | 1/2010 | Rankers | ............. | A61B 5/14532 600/365 |
| 2010/0049164 A1 | 2/2010 | Estes et al. | | |
| 2010/0069890 A1* | 3/2010 | Graskov | ............. | G06F 19/3406 604/890.1 |
| 2011/0193704 A1* | 8/2011 | Harper | ............... | A61B 5/14532 340/573.1 |
| 2012/0130646 A1* | 5/2012 | Landis | ................ | G06F 19/3406 702/19 |
| 2012/0245447 A1* | 9/2012 | Karan | ................ | A61B 5/14532 600/365 |
| 2013/0297330 A1 | 11/2013 | Kamen et al. | | |
| 2013/0338465 A1* | 12/2013 | Taub | ................. | A61B 5/14532 600/365 |
| 2014/0347186 A1* | 11/2014 | Harper | ............... | A61B 5/14532 340/573.1 |
| 2014/0364175 A1* | 12/2014 | Kim | .................... | H04W 52/027 455/574 |

* cited by examiner

DEVICES AND METHODS FOR CONTINUOUS ANALYTE MONITORING

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 61/904,341, filed Nov. 14, 2013. The aforementioned application is incorporated by reference herein in its entirety, and is hereby expressly made a part of this specification.

TECHNICAL FIELD

The present embodiments relate to continuous analyte monitoring, and more particularly to apparatus and methods for providing information in a continuous analyte monitoring system.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood glucose, which can cause an array of physiological derangements associated with the deterioration of small blood vessels, for example, kidney failure, skin ulcers, or bleeding into the vitreous of the eye. A hypoglycemic reaction (low blood glucose) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter that transmits measurement data to a receiver that processes and displays information based on the measurements. Such sensor systems are sometimes referred to as continuous glucose monitors (CGMs).

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In a first aspect, which is generally applicable (i.e. independently combinable with any of the aspects or embodiments identified herein), particularly with any other embodiment of the first aspect, certain of the present embodiments comprise a wearable device for providing information to a user regarding the user's blood glucose value, the device comprising: a communication module for receiving a signal from a continuous glucose monitoring (CGM) system; and a display configured to display information based on the received signal for a set duration.

In an embodiment of the first aspect, the signal is received from a receiver of the CGM system.

In an embodiment of the first aspect, the receiver is a smartphone.

In an embodiment of the first aspect, the information displayed includes at least one of a glucose value, a glucose trend, an alert, and a time when the signal was received from the CGM system.

In an embodiment of the first aspect, the device further comprises a timer.

In an embodiment of the first aspect, the timer measures the set duration.

In an embodiment of the first aspect, the display is configured to cease displaying the information after the set duration elapses.

In an embodiment of the first aspect, after the set duration elapses no further information can be displayed on the display until the communication module receives another signal from the CGM system.

In an embodiment of the first aspect, the set duration begins when the signal is received from the CGM system.

In an embodiment of the first aspect, the display of the information commences without any user interaction.

In an embodiment of the first aspect, a brightness of the displayed information fades as the set duration elapses.

In an embodiment of the first aspect, the set duration is in the range of one second to twenty minutes.

In an embodiment of the first aspect, the device further comprises an input device for enabling the user to acknowledge that the information has been viewed.

In an embodiment of the first aspect, when the user acknowledges that the information has been viewed, the communication module sends an acknowledgement signal to the CGM system.

In an embodiment of the first aspect, the display comprises electronic paper, electronic ink, an electrophoretic display, a gyricon, a liquid crystal display (LCD), one or more light-emitting diodes (LEDs), one or more organic light-emitting diodes (OLEDs), a color- or pattern-changing material, magnetic materials, piezo-electric materials, vibration patterns, heat/cold patterns, one or more light pipes with single-color or multicolor LED(s) or OLED(s), a transparent and flexible multi-touch surface, or an interactive glass surface.

An embodiment of the first aspect further comprises a band configured to be worn about a wrist of a wearer, wherein the communication module and the display are incorporated into the band.

In an embodiment of the first aspect, the device further comprises a status flag that indicates when the device last received the signal from the CGM system.

In a second aspect, which is generally applicable (i.e. independently combinable with any of the aspects or embodiments identified herein), particularly with any other embodiment of the second aspect, certain of the present embodiments comprise a method of providing information to a user regarding the user's blood glucose value, the method comprising: receiving a signal providing information about the user's current blood glucose value; and displaying the information based on the received signal for a set duration.

In an embodiment of the second aspect, the signal is received from a receiver of a continuous glucose monitoring (CGM) system.

In an embodiment of the second aspect, the receiver is a smartphone.

In an embodiment of the second aspect, the information displayed includes at least one of a glucose value, a glucose trend, an alert, and a time when the signal was received.

An embodiment of the second aspect further comprises a timer measuring the set duration.

An embodiment of the second aspect further comprises ceasing displaying the information after the set duration elapses.

In an embodiment of the second aspect, after the set duration elapses no further information can be displayed until another signal is received.

In an embodiment of the second aspect, the set duration begins when the signal is received.

In an embodiment of the second aspect, the display of the information commences without any user interaction.

An embodiment of the second aspect further comprises a brightness of the displayed information fading incrementally as the set duration elapses.

In an embodiment of the second aspect, the set duration is in the range of one second to twenty minutes.

An embodiment of the second aspect further comprises receiving an input acknowledging that the information has been viewed.

An embodiment of the second aspect further comprises sending an acknowledgement signal.

An embodiment of the second aspect further comprises ceasing displaying the information upon receiving the input acknowledging that the information has been viewed.

In a third aspect, which is generally applicable (i.e. independently combinable with any of the aspects or embodiments identified herein), particularly with any other embodiment of the third aspect, certain of the present embodiments comprise a wearable device for providing information to a user regarding the user's blood glucose value, the device comprising: a communication module for receiving a signal from a continuous glucose monitoring (CGM) system; and a display configured to display information based on the received signal in response to an input from the user.

In an embodiment of the third aspect, the input is at least one of user motion, a voice command from the user, and a retinal input from the user.

In a fourth aspect, which is generally applicable (i.e. independently combinable with any of the aspects or embodiments identified herein), particularly with any other embodiment of the fourth aspect, certain of the present embodiments comprise a system for providing information to a user regarding the user's blood glucose value, the system comprising: a first electronic device including a first communication module for receiving a first signal from sensor electronics and a display configured to display information based on the received first signal; and a second electronic device including a second communication module for receiving a second signal from the sensor electronics.

In an embodiment of the fourth aspect, the first electronic device is a wearable device.

In an embodiment of the fourth aspect, the wearable device is a bracelet, an anklet, glasses, a ring, a necklace, an arm band, a pendant, a belt clip, a hair clip, a hair tie, a pin, a cufflink, a tattoo, a sticker, a sock, a sleeve, a glove, a garment, a zipper pull, a button, a watch, a shoe, a contact lens, a subcutaneous implant, a cochlear implant, a shoe insert, a brace for teeth, a body brace, a medical wrap, a wristband, a headband, a hat, a bandage, a hair weave, nail polish, an artificial joint, an artificial body part, an orthopedic pin, an orthopedic device, an implantable cardiac device, or an implantable neurological device.

In an embodiment of the fourth aspect, the second electronic device is a smartphone.

In a fifth aspect, which is generally applicable (i.e. independently combinable with any of the aspects or embodiments identified herein), particularly with any other embodiment of the fifth aspect, certain of the present embodiments comprise a method of providing information to a user regarding the user's blood glucose value. The method comprises: transmitting a first signal using a continuous analyte monitoring system, the first signal comprising alert and/or glucose value information; and if an acknowledgment of the information of the first signal is not received within a preset time limit, transmitting a second signal, the second signal comprising the information or an updated version of the information.

In an embodiment of the fifth aspect, the first signal is specifically directed to a first electronic device, wherein the acknowledgement comprises detecting user input indicative of the user receiving the information.

In an embodiment of the fifth aspect, the information is displayed on a display of the first electronic device or an audible or vibratory alert is programmatically triggered by the first electronic device responsive to the information.

In an embodiment of the fifth aspect, the user input comprises one or more of a user selecting a prompt on a touch sensitive screen of the first device, a user depressing a button on the first device, the first device detecting a predefined user motion of the first device and the first device detecting a predefined retinal characteristic of the user.

In an embodiment of the fifth aspect, the first electronic device is a smart phone.

In an embodiment of the fifth aspect, the first device comprises a wearable device, and wherein the wearable device is a bracelet, an anklet, glasses, a ring, a necklace, an arm band, a pendant, a belt clip, a hair clip, a hair tie, a pin, a cufflink, a tattoo, a sticker, a sock, a sleeve, a glove, a garment, a zipper pull, a button, a watch, a shoe, a contact lens, a subcutaneous implant, a cochlear implant, a shoe insert, a brace for teeth, a body brace, a medical wrap, a wristband, a headband, a hat, a bandage, a hair weave, nail polish, an artificial joint, an artificial body part, an orthopedic pin, an orthopedic device, an implantable cardiac device, or an implantable neurological device.

In an embodiment of the fifth aspect, the second signal is specifically directed to a second electronic device.

In an embodiment of the fifth aspect, the second signal is generated and transmitted using the continuous analyte system, and wherein the first electronic device is configured to generate and transmit an acknowledgement signal to the continuous analyte system responsive to detecting user acknowledgement of the information.

In an embodiment of the fifth aspect, the second signal is generated and transmitted using the first electronic device.

In an embodiment of the fifth aspect, the second electronic device displays information based on the received second signal.

In an embodiment of the fifth aspect, the second electronic device is a smartphone.

In an embodiment of the fifth aspect, the second electronic device is a wearable device.

In a sixth aspect, which is generally applicable (i.e. independently combinable with any of the aspects or embodiments identified herein), particularly with any other embodiment of the sixth aspect, certain of the present embodiments comprise a device substantially as shown and/or described in the specification and/or drawings.

In a seventh aspect, which is generally applicable (i.e. independently combinable with any of the aspects or embodiments identified herein), particularly with any other embodiment of the seventh aspect, certain of the present embodiments comprise a method substantially as shown and/or described in the specification and/or drawings.

In an eighth aspect, which is generally applicable (i.e. independently combinable with any of the aspects or embodiments identified herein), particularly with any other embodiment of the eighth aspect, certain of the present embodiments comprise a system substantially as shown and/or described in the specification and/or drawings.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and non-obvious devices and methods shown in the accompanying drawings, which are for illustrative purposes only. These drawings include the following figures, in which like numerals indicate like parts.

DETAILED DESCRIPTION

Figure 1:
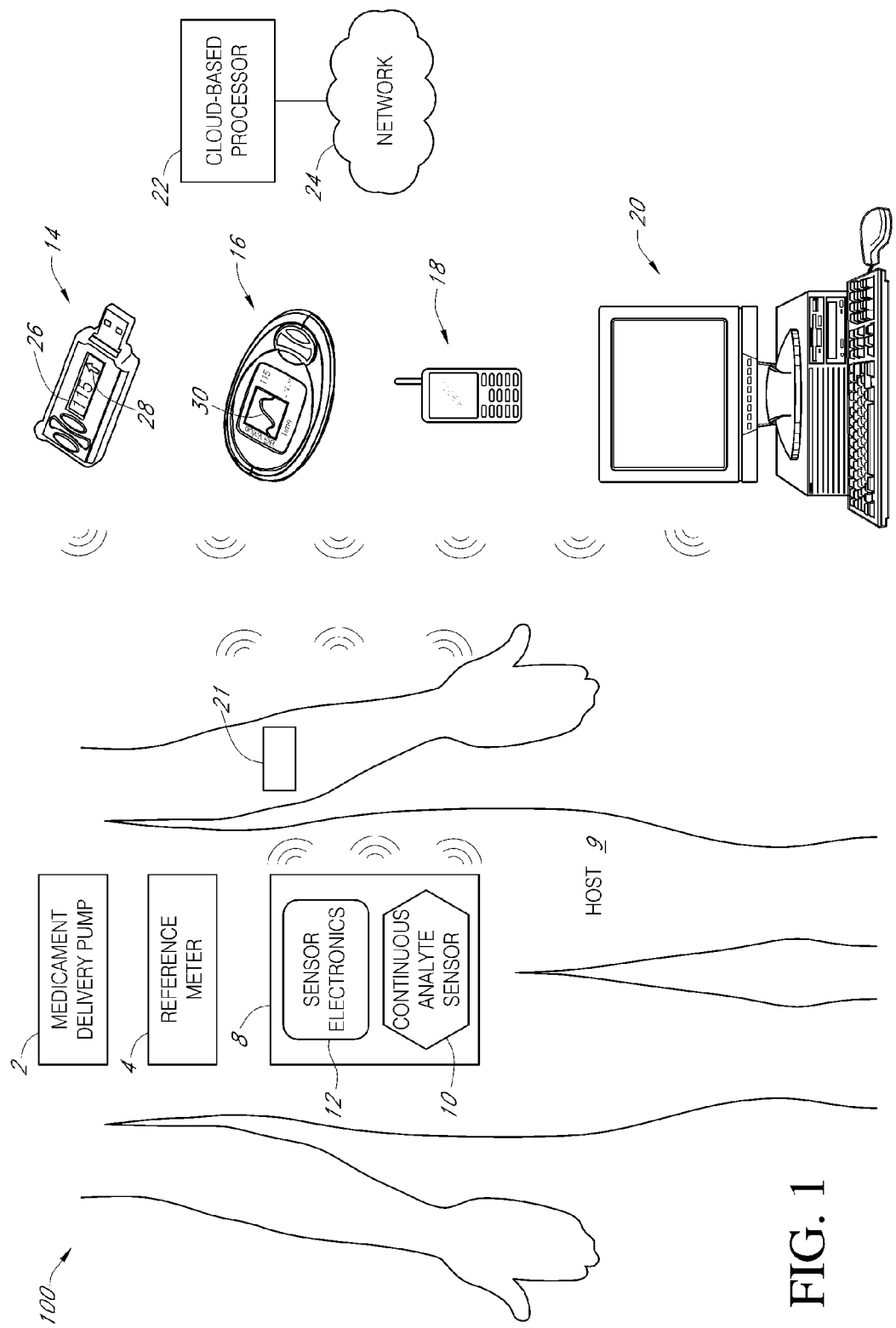
FIG. 1 is a schematic view of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features.

The drawings and their descriptions may indicate sizes, shapes and configurations of the various components. Such depictions and descriptions should not be interpreted as limiting. Alternative sizes, shapes and configurations are also contemplated as within the scope of the present embodiments. Also, the drawings, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

The embodiments relate to the use of an analyte sensor that measures a concentration of glucose or a substance indicative of the concentration or presence of the analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods described herein can be applied to any measurable analyte. In embodiments, the analyte sensor is a glucose sensor capable of measuring the concentration of glucose in a host. Examples described below include an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Application Publication No. 2011/0027127, or a transcutaneous glucose sensor, such as described with reference to U.S. Patent Application Publication No. 2006/0020187, or a dual electrode analyte sensor, such as described with reference to U.S. Patent Application Publication No. 2009/0137887, or is configured to be implanted in a host vessel or extracorporeally, such as is described in U.S. Patent Application Publication No. 2007/0027385.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies; acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hematocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; anti-pyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyl-transferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

For illustrative purposes, reference will now be made to FIG. 1, which is an example environment in which some embodiments described herein may be implemented. Here, an analyte monitoring system 100 includes a continuous analyte sensor system 8 coupled to a host 9. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate from the sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18, 20, and/or one or more wearable devices 21.

The system 100 of FIG. 1 also includes a cloud-based processor 22 configured to analyze analyte data, medicament delivery data, and/or other patient related data provided over network 24 directly or indirectly from one or more of sensor system 8, medicament delivery pump 2, reference analyte meter 4, display devices 14, 16, 18, 20, and wearable device 21. Based on the received data, the processor 22 can further process the data, generate reports providing information based on the processed data, trigger notifications to electronic devices associated with the host 9 or a caretaker of the host 9, and/or provide processed information to any of the other devices of FIG. 1. In some example implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

Although the example implementation described with respect to FIG. 1 refers to analyte data being received by processor 22, other types of data processed and raw data may be received as well.

In some example implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, 20, and wearable device 21. The display devices 14, 16, 18, 20 may be configured for processing and presenting information, such as sensor information transmitted by the sensor electronics module 12 for display at the display device. The display devices 14, 16, 18, 20, and/or the wearable device 21 may also trigger alarms based on the analyte sensor data.

The wearable device 21 may also be configured for processing and presenting information, such as sensor information transmitted by the sensor electronics module 12. The processing and presenting of such information is described in greater detail below with respect to algorithms and systems implementing such algorithms, e.g., as detailed in FIGS. 4-7. The wearable device 21 may include an alert interface. The alert interface may comprise, for example, a physical device such as a display, a vibration module, a shock module, a speaker, and/or any other type of device that is capable of providing the user with physiological information and/or an alert.

In FIG. 1, display device 14 is a key fob-like display device, display device 16 is a hand-held application-specific computing device 16 (e.g., the DexCom G4® Platinum receiver commercially available from DexCom, Inc.), display device 18 is a general purpose smartphone or tablet computing device (e.g. Android®-based devices, or an Apple® iPhone®, iPad®, or iPod Touch® commercially available from Apple, Inc.), display device 20 is a computer workstation, and wearable device 21 is any device that is worn on, or integrated into, a user's vision, clothes, and/or bodies. In some example implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. In some example implementations, the wearable device 21 may comprise anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. The small display device 14 and/or the wearable device 21 may include a relatively small display (e.g., smaller than the display device 18) and may be configured to display graphical and/or numerical representations of sensor information, such as a numerical value 26 and/or an arrow 28. In contrast, the display devices 16, 18, and 20 can be larger display devices that can be capable of displaying a larger set of displayable information, such as a trend graph 30 depicted on the hand-held receiver 16 in addition to other information such as a numerical value and arrow.

In various embodiments, the wearable device 21 may be attached to the wearer and/or to his or her clothing in any convenient fashion. For example, the wearable device 21 may encompass a body part of the wearer, such as an arm, a leg, the neck, etc. Instead, or in addition, the wearable device 21 may be secured to the wearer's skin with adhesive. In embodiments including a vibration module, a shock module, or any other device that provides the wearer with tactile feedback, these embodiments may be most effective if the wearable device 21 is directly or indirectly touching the wearer's skin in such a way that vibrations, shocks, etc. can be felt by the wearer. For example, directly securing the wearable device 21 to the wearer's skin with adhesive may be advantageous.

It is understood that any other user equipment (e.g. computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some example implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may comprise any device capable of measuring the concentration of glucose and may use a variety of techniques to measure glucose including invasive, minimally invasive, and non-invasive sensing techniques (e.g., fluorescent monitoring), to provide data, such as a data stream, indicative of the concentration of glucose in a host, and in many cases in the form of counts. The data stream may be a raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). That is, the raw data in the form of counts is converted into a data form usable by the host or a caregiver, using a conversion algorithm that takes account of the calibration. For example if 2000 counts corresponds to a glucose concentration value of 100 mg/dL, as measured by a calibration device known to be accurate, then such and other calibration readings may be employed to convert other readings from counts to glucose concentration values.

The continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

Figure 2:
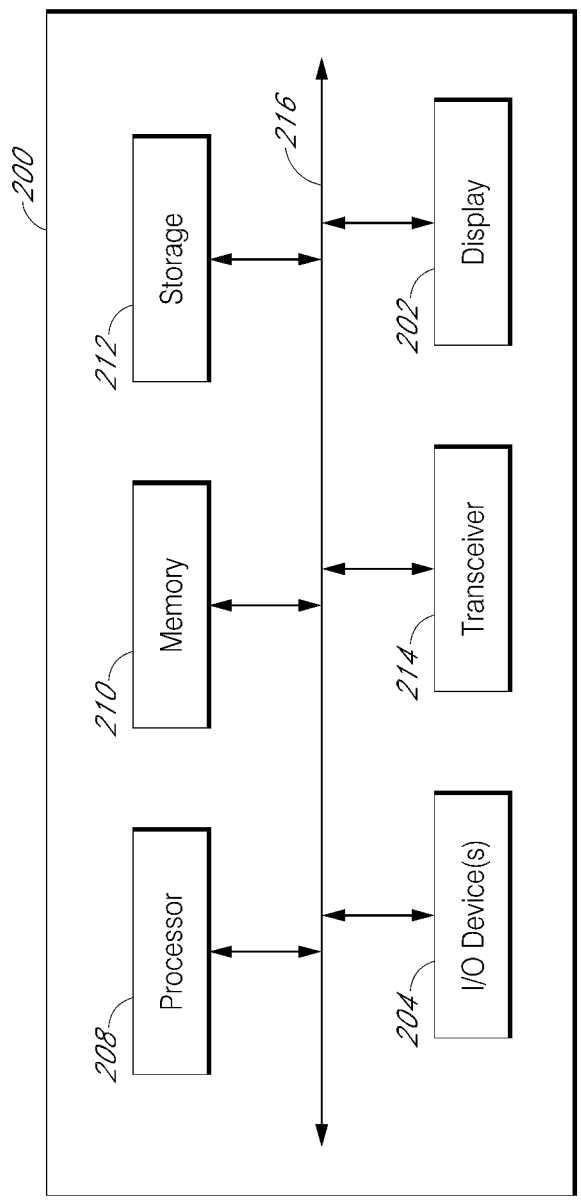
FIG. 2 is a functional block diagram of one of the display devices of FIG. 1.

FIG. 2 is a block diagram of an electronic device 200, illustrating its functional components in accordance with some embodiments. The electronic device 200 may be any of the electronic devices mentioned herein, such as any of the display devices discussed in FIG. 1 in addition to any other receiver of a CGM system, smartwatch, tablet computer, mini-tablet computer, handheld personal data assistant (PDA), game console, multimedia player, wearable device, such as those described above, screen in an automobile, etc., and/or incorporate the functionality of any or all of the other electronic devices, including wherein some or all of the functionally is embodied on a remote server.

With reference to FIG. 2, the electronic device 200 includes a display 202 and one or more input/output ("I/O") device(s) 204, such as one or more buttons and/or switches. The display 202 may be any device capable of displaying output, such as an LCD or LED screen and others, and may comprise a touchscreen. The I/O devices 204 may comprise, for example, a keyboard, one or more buttons, one or more switches, etc. In embodiments including a touchscreen, the display 202 also functions as an I/O device 204.

The electronic device 200 further includes a processor 208 (also referred to as a central processing unit (CPU)), a memory 210, a storage device 212, a transceiver 214, and may include other components or devices (not shown). The memory 210 is coupled to the processor 208 via a system bus or a local memory bus 216. The processor 208 may be, or may include, one or more programmable general-purpose or special-purpose microprocessors, digital signal processors (DSPs), programmable controllers, application specific integrated circuits (ASICs), programmable logic devices (PLDs), or the like, or a combination of such hardware-based devices.

The memory 210 provides the processor 208 access to data and program information that is stored in the memory 210 at execution time. Typically, the memory 210 includes random access memory (RAM) circuits, read-only memory (ROM), flash memory, or the like, or a combination of such devices.

The storage device 212 may comprise one or more internal and/or external mass storage devices, which may be or may include any conventional medium for storing large volumes of data in a non-volatile manner. For example, the storage device 212 may include conventional magnetic disks, optical disks, magneto-optical (MO) storage, flash-based storage devices, or any other type of non-volatile storage devices suitable for storing structured or unstructured data. The storage device 212 may also comprise storage in the "cloud" using so-called cloud computing. Cloud computing pertains to computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction.

The electronic device 200 may perform various processes, such as, for example, correlating data, pattern analysis, and other processes. In some embodiments, the electronic device 200 may perform such processes on its own. Alternatively, such processes may be performed by one or more other devices, such as one or more cloud-based processors 22 described above. In still further embodiments, these processes may be performed in part by the electronic device 200 and in part by other devices. Various example processes are described herein with reference to the electronic device 200. These example processes are not limited to being performed by the display device 18 alone. Further, as used herein, the term "electronic device" should be construed to include other devices with which the electronic device 200 interacts, such as one or more cloud-based processors 22, servers, etc. The electronic device 200 may also include other devices/interfaces for performing various functions, details of which are not germane to the inventive embodiments described herein.

The transceiver 214 enables the electronic device 200 to communicate with other computing systems, storage devices, and other devices via a network. While the illustrated embodiment includes a transceiver 214, in alternative embodiments a separate transmitter and a separate receiver may be substituted for the transceiver 214.

In some embodiments, the processor 208 may execute various applications, for example, a CGM application, which may be downloaded to the electronic device 200 over the Internet, such as from iTunes®, Google Play®, etc., and/or a cellular network, and the like. Data for various applications may be shared between the electronic device 200 and one or more other devices/systems, and stored by storage 212 and/or on one or more other devices/systems.

In certain embodiments, the sensor of the continuous analyte monitoring system 8 of FIG. 1 is inserted into the skin of the host 9. A new sensor session is then initiated with the sensor, the transmitter, and the electronic device. The embodiments described herein contemplate numerous techniques for initializing the sensor. For example, initialization may be triggered when the sensor electronics engages the sensor. In another example, initialization may be triggered by a mechanical switch, such as a switch (not shown) on a snap-in base that receives the sensor electronics. When the sensor electronics are snapped into the base, the switch is automatically tripped. In another example, initialization may be menu driven, as the user may be prompted by a user interface of the display device 18 of FIG. 1 to begin initialization by making a selection on the user interface, such as by pushing a button or touching a designated area on a touchscreen. In another example involving a non-invasive sensor that is applied to the wearer's skin, the sensor may sense when it is in contact with skin and start automatically. Further, the analyte sensor system can detect use of a new sensor using any of the above techniques, automatically prompt the user to confirm the new sensor session by way of a prompt on a user interface of the system, and initiate an initialization response to the user confirmation responsive to the prompt. Additional examples of initializing the sensor are found in U.S. patent application Ser. No. 13/796,185, filed on Mar. 12, 2013, the entire disclosure of which is hereby incorporated by reference herein.

In some CGM systems, sensor data is displayed on a handheld receiver, which may be a dedicated device (used for CGM only) or may have other functionality. For example, the receiver may be a smartphone that executes a CGM application (which may also be referred to as an "app"). With such systems, the user typically must locate the receiver in order to view sensor data. Sometimes the task of locating the receiver can be bothersome, such as when the receiver is contained in a purse with numerous other items, or is buried deep in the user's pocket. Even when the receiver is close at hand, viewing sensor data may still be cumbersome, such as when the user has to unlock a display of the device (as is typical with many smartphones) in order to view data, and/or when the user has to navigate through multiple screens or a complicated user interface to access and obtain the desired data.

Embodiments described herein provide solutions to these problems by providing "zero-click" viewing of CGM data. In various embodiments, no touching or button pressing is required. The display with sensor data may be "always on." These embodiments enable discrete viewing of sensor data without significant user hassle. The user can glance at sensor data at any time, without any burdensome steps being required.

Figure 3:
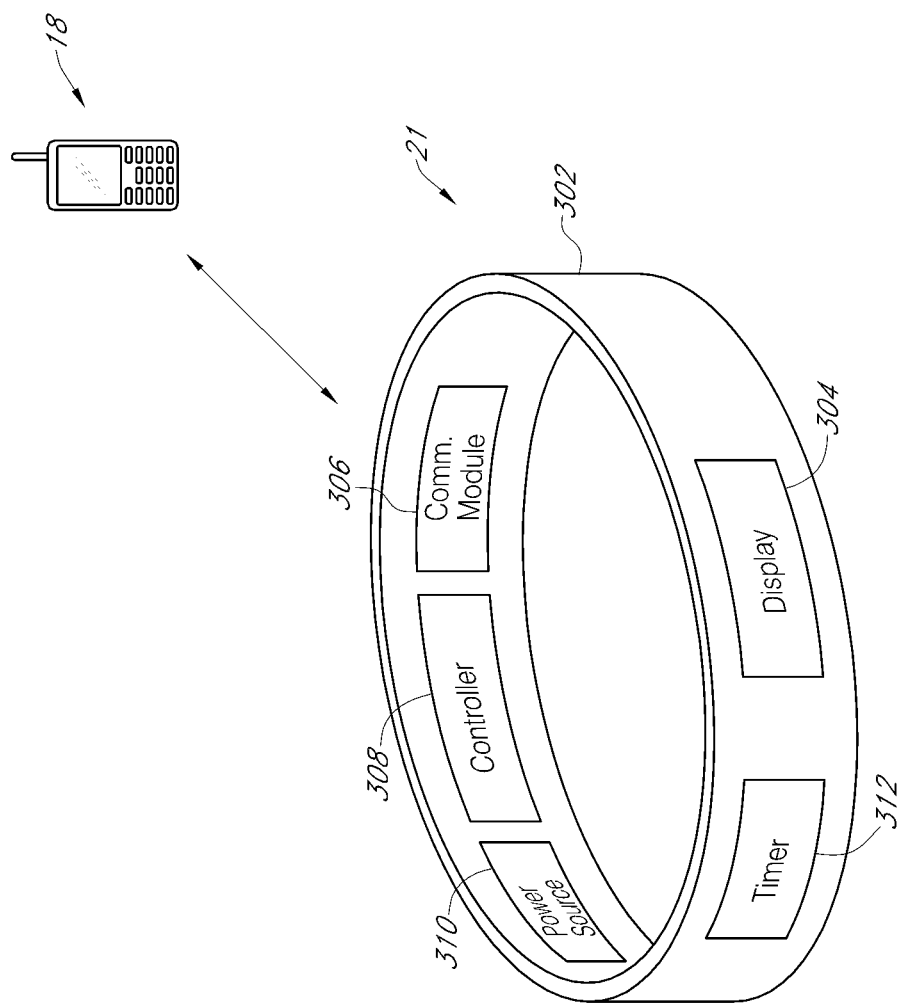
FIG. 3 is a front perspective view of a wearable device according to the present embodiments.

With reference to FIG. 3, some of the present embodiments comprise a wearable device 21. The wearable device 21 may comprise any of the wearable devices described herein, including those described above with respect to FIGS. 1 and 2. However, for ease of explanation, the illustrated embodiment of the wearable device 21 comprises a closed loop band 302 having no endpoints and sized to be comfortably worn about the wrist. The band 302 may be constructed of flexible and resilient material such that it can stretch to be slipped over the hand. Example materials include rubbers of various types (e.g. vulcanized, butadiene, etc.), silicone, latex, nylon, polyester, leather, steel, string/cord, other plastics (acrylic, polycarbonate, polyesters, polyethylene, polypropylene, ABS, etc.), ceramic, etc. In alternative embodiments, the band 302 may not be a closed loop. Instead, the band 302, made from any material, may comprise first and second ends that are releasably securable to one another with a buckle, clasp, etc.

The wearable device 21 comprises a display 304 that is configured to display information about one or more of the wearer's physiologic conditions. For example, the display 304 may be configured to receive and display sensor data from the sensor system 8 (FIG. 1), including glucose values, glucose trend information, alerts, etc., based on a signal received from the sensor system 8 and/or another device. In one example, glucose and activity levels may be combined in a simple display to aid diabetics and/or athletes in managing glucose levels. The examples described herein relate to the user's blood glucose, but the present embodiments are not limited to these examples, and could include any physiologic conditions or combinations of conditions. In some embodiments the information displayed on the display 304 may also include a time, such as a time when the latest signal from the sensor system 8 was received.

The display 304 may comprise, for example, any type of display, including but not limited to a liquid crystal display (LCD), one or more light-emitting diodes (LEDs), one or more organic light-emitting diodes (OLEDs), an electronic paper display, an electrophoretic display, a gyricon, e-ink, a color- or pattern-changing material, magnetic materials, piezo-electric materials, vibration patterns, heat/cold patterns, one or more light pipes with single-color or multicolor LED(s) or OLED(s), transparent and flexible multi-touch surfaces, such as those available from 3M, interactive glass surfaces, such as those available from Corning, etc. The display 304 may have a plurality of addressable segments configured to allow the formation of letters, numbers, and other shapes. Accordingly, in some embodiments, sensor data and optionally time signals may be transformed by the wearable device 21 into the addresses of the segments to be biased. A conductive matrix layer receives the signal and biases the display accordingly, for example to show a glucose value and/or a trend arrow. In some embodiments a time may also be displayed, such as a current time, a time at which the signal was received, a time at which sensor data encoded in the signal was measured, etc. In further embodiments, the wearable device may not include a discrete display. Rather, the wearable device itself may be a display that presents information by, for example, changing the color of the entire wearable device. Further examples of displays that may be included in any of the present embodiments are described in U.S. Pat. Nos. 5,808,783 and 6,118,426, which are incorporated herein by reference in their entireties and made part of this disclosure.

The wearable device 21 may further include a button (not shown) to activate and/or deactivate the display 304. A button could also be provided to power down the wearable device. Powering down may be useful during activities where the user knows his or her blood glucose is likely to rise or fall significantly, and does not want to be alarmed. For example, before and/or during exercise a user may preemptively take insulin or eat food to correct for an expected change in blood glucose, and the user may therefore want to clear any alarms or turn the wearable device 21 off altogether.

The wearable device 21 further comprises a communication module 306, which enables the wearable device 21 to receive information about the user's blood glucose from the sensor electronics unit 12 of the sensor system 8 (FIG. 1), and/or from another device, such as the smartphone 18. The communication module 306 may include an antenna (not shown) and any other hardware and circuitry necessary for receiving and processing received signals. The communication module 306 may comprise a transceiver 214 (FIG. 2) having both transmit and receive capabilities, and/or a receiver and a transmitter as separate components.

The wearable device 21 further comprises a controller 308 for controlling operation of the display 304 and the communication module 306. The controller 308 may include one or more of a processor, a microprocessor, a programmable logic controller, an application specific integrated circuit (ASIC), a system on a chip (SoC), a programmable system-on-chip (PSoC), etc. The wearable device 21 further comprises a power source 310, such as a battery, for powering the display 304, the communication module 306, and/or the controller 308. In some embodiments, the power source 310 may be a rechargeable and/or replaceable battery. In one particular embodiment, the battery may be recharged via a universal serial bus (USB) connection (not shown) that also allows information to be transferred from the wearable device 21 to another device, such as the computing device 20 (FIG. 1).

The wearable device 21 may be further configured to display information from the sensor system 8 without requiring an input from the wearer. In such embodiments, which may be referred to as "zero-click" embodiments, the display 304 displays information from the sensor system 8 immediately upon receiving a signal from the sensor system 8, or after a pre-programmed delay (or after a short delay necessitated by processing of the signal information by the wearable device 21), and without the need for the wearer (or any other person) to touch the wearable device 21, or press a button on the wearable device 21, etc. The display 304 in zero-click embodiments may be an "always on" type of display, in which information from the sensor system 8 is always displayed on the display 304. However, as described further below, the information displayed on the display 304 may fade over time and/or disappear after a given interval has elapsed.

Zero-click embodiments advantageously enable the wearer of the wearable device 21 to discreetly view his or her current glucose information by merely glancing at the wearable device 21, thereby reducing the burden to the wearer. When the wearer wants to view updated glucose information, there is no need for him or her to search in his or her pockets or purse to locate a handheld receiver of a CGM system, or to unlock his or her smartphone (where a smartphone is used to display glucose information in a CGM system).

Figure 4:
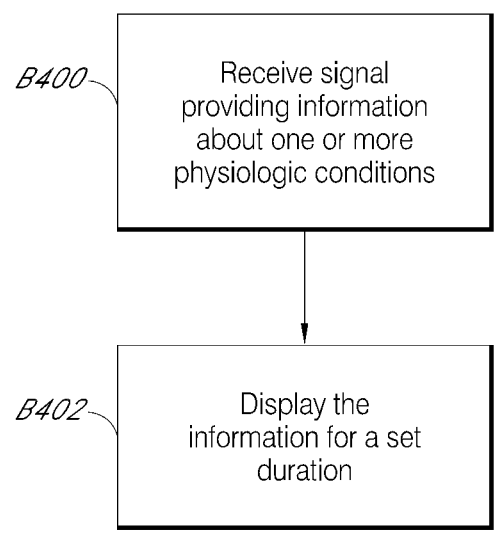
FIGS. 4-7 are flowcharts of processes according to the present embodiments.
Figure 5:
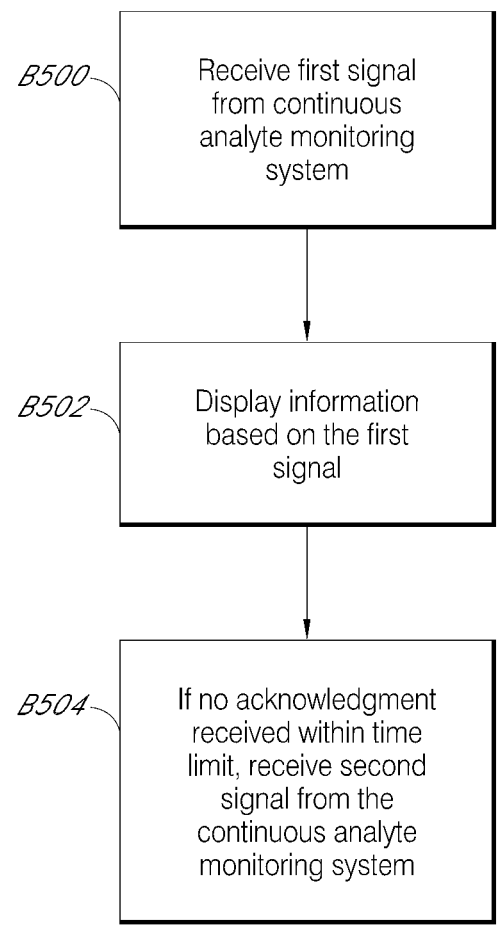

As described above, the display 304 of the wearable device 21 may be configured to display information for only a set duration. With reference to FIG. 4, upon receiving a signal (box B400) from the sensor electronics unit 12 of the sensor system 8, and/or from another device, such as the smartphone 18, information encoded in the signal is displayed on the display 304, and after a set interval has elapsed, the information disappears (box B402). For example, the wearable device 21 may include a timer 312, as shown in FIG. 3. The timer 312 may begin running in response to a trigger, such as when the wearable device 21 receives a signal from the sensor system 8, or when new information is first displayed on the display 304. When the set interval has elapsed, as measured by the timer 312, the information on the display 304 may disappear. The length of the interval may be pre-programmed and stored in memory of the wearable device 21. The length of the pre-programmed interval may be any length. For example, the length of the interval may be in the range from 1 second to 30 minutes, such as 1 minute, 2 minutes, 3 minutes, 5 minutes, 10 minutes, 15 minutes, 30 minutes, etc.

In some embodiments, the timer 312 may be omitted, but the information on the display 304 may still disappear after a set interval has elapsed due to an electrical charge powering the display discharging over time. The length of the interval that elapses between the display 304 illuminating with new sensor information and the display 304 completely darkening can be tailored to be any length. For example, the length of the interval may be 1 minute, 2 minutes, 3 minutes, 5 minutes, 10 minutes, 15 minutes, 30 minutes, etc.

In some embodiments, after a given set of sensor information fades or disappears from the display 304, it cannot reappear. For example, at time $t_0$ the wearable device 21 may receive signal A from the sensor system 8, and information encoded in signal A is then displayed on the display 304. The information then persists on the display 304 for a set interval N. At time $t_N$, the information encoded in signal A disappears from the display 304. The information encoded in signal A cannot subsequently be shown on the display 304 in some implementations. This functionality can ensure that the wearer only views a most up-to-date sensor data value. This functionality can also ensure that the wearer does not mistake stale data for current data in the event that communication between the sensor electronics 12 and the wearable device 21 is interrupted. For example, if the CGM system only supports one-way communication between the sensor electronics 12 and the wearable device 21, i.e., signals can be transmitted from the sensor electronics 12 to the wearable device 21, but not from the wearable device 21 to the sensor electronics 12, the wearer may be unaware that communication between the sensor electronics 12 and the wearable device 21 has been interrupted. If the wearable device 21 continues to display, or displays for an indefinite length of time, data received prior to interruption of the communication between the sensor electronics 12 and the wearable device 21, the wearer may believe that the displayed data is current, when in fact it is stale. Displaying a given set of data for only a set interval can solve this problem.

With further reference to FIG. 3, and as described above, in some embodiments the communication module 306 may have both receive and transmit capabilities, such that the wearable device 21 may transmit information to one or more other devices. In FIG. 3, only one other device (the smartphone 18 of FIG. 1) is illustrated, but embodiments are not limited to this example. The communication module 306 may send signals to any type of other device, including any of those shown and described with respect to FIG. 1.

In embodiments in which the communication module 306 has both receive and transmit capabilities, the wearable device 21 may transmit an acknowledgement to the sensor system 8 after the wearer has viewed information transmitted by the sensor system 8 to the wearable device 21. For example, with reference to FIG. 5, the wearable device 21 may receive a signal from the sensor system 8 (box B500), and information encoded in the signal is then displayed on the display 304 (box B502). After the wearer views the information, he or she may press a button on the wearable device 21, or perform any other action indicating to the wearable device 21 that the information has been viewed. The wearable device 21 may then send a signal back to the sensor system 8 to acknowledge that the information has been viewed. This functionality is particularly advantageous when the sensor information indicates that the wearer's glucose is dangerously high or low, or is trending dangerously high or low. In such situations, if the wearer does not acknowledge that he or she has viewed the information, the sensor system may take additional steps, such as providing one or more alerts to the wearer and/or to one or more third parties (box B504). The wearable device 21 also may, or may not, cease displaying the information when the wearer acknowledges having viewed the information.

In some embodiments, the display 304 may activate in response to various types of stimuli. For example, the wearable device 21 may include an accelerometer, or another device for detecting motion. When the wearable device 21 detects motion of the wearer, the dormant display 304 may activate to display the most up-to-date sensor information. In another example, the wearable device 21 may include a microphone and any circuitry necessary to enable voice control. When the wearable device 21 detects a voice command from the wearer, the dormant display 304 may activate to display the most up-to-date sensor information. In another example, the wearable device 21 may include a sensor for detecting a retinal input (detecting when the wearer is looking at the wearable device 21). When the wearable device 21 detects that the wearer is looking at it, the dormant display 304 may activate to display the most up-to-date sensor information.

In some embodiments, the wearable device 21 may be configured to provide alerts from the sensor system and also from other systems (non-CGM systems). For example, the wearable device 21 may be configured to receive signals from one or more social networks. In such embodiments, the wearable device 21 may be configured to prioritize CGM alerts over other types of alerts so that the wearer is more likely to receive CGM alerts.

In some embodiments, the wearable device 21 may include a system status indicator that informs the wearer whether the wearable device 21 is currently communicating with the sensor system 8. For example, if the wearable device 21 is receiving signals from the sensor system 8 as expected, the display 304 may show an "active" or "normal" status flag. But if the wearable device 21 is not receiving signals from the sensor system 8 as expected, the display 304 may show an "inactive" status flag, or show no status flag at all. For example, if the sensor system 8 is supposed to send updated information to the wearable device 21 every 30 minutes, the status flag may change from active to inactive (or disappear) after 30 minutes have elapsed since the wearable device 21 received the last signal from the sensor system 8. The wearer, upon noticing that the status flag is inactive (or not visible), may then take corrective action, such as troubleshooting the lack of communication between the wearable device 21 and the sensor system 8.

As described above, the display 304 may comprise any of a variety of types of displays. The display 304 may be configured to provide different types/amounts of information and/or one or more alerts. For example, the display's functionality may be limited to simply changing color in response to the signal received from the sensor electronics unit 12, such as displaying a first color, such as green, when the signal indicates that the user's blood glucose is within an acceptable range, and displaying a second color, such as red, when the signal indicates that the user's blood glucose is outside the acceptable range. The color changing functionality may also be further refined to include more colors, such as displaying a first color, such as green, when the signal indicates that the user's blood glucose is within a first narrower range, displaying a second color, such as yellow, when the signal indicates that the user's blood glucose is outside the first narrower range, but still within a second wider range, and displaying a third color, such as red, when the signal indicates that the user's blood glucose is outside the second wider range.

In a further embodiment, an output of the display 304 may be more discreet and pre-programmed by the user. For example, when one of the low or high thresholds is breached, a first user-programmed pattern may be displayed, and when the other of the low or high thresholds is breached, a second pattern is revealed. The patterns may be customized by the user so that the meaning of each pattern is only known to the user. This embodiment enhances the discreetness of the wearable device 21 because no one else, other than the user, knows the state of the user's glucose.

In the foregoing embodiments, the simplicity and limited functionality of the display 304 reduce the cost and complexity of the wearable device 21, while still providing certain types of users, such as those with type 2 diabetes, with adequate information to manage their condition. In alternative embodiments, the limited functionality of the display 304 may be embodied in something other than a changing color, such as displaying nothing more than a trend arrow (e.g. an arrow indicating whether the user's current blood glucose value is rising or falling, where the arrow points upward to indicate a rising value and downward to indicate a falling value), nothing more than text such as "high," "normal," and/or "low" to indicate the user's current blood glucose value, nothing more than text such as a number corresponding to the user's current blood glucose value, where the number may be color coded (e.g. green for normal, red for high or low) or not, or providing one or more lights that remain solid or blink in response to various conditions. For example, three lights, such as LEDs may be provided, of the same color or different colors. A single blinking light may indicate a hypoglycemic condition, a single solid light may indicate a low glucose condition, two solid lights may indicate that glucose is in the target range, three solid lights may indicate a high glucose condition, and three blinking lights may indicate a hyperglycemic condition. In another example, a progression of lights illuminating may indicate a level of clinical risk, severity of hypo- or hyper-glycaemia, rate of change of glucose, etc. For example, lights flashing from left to right or bottom to top may indicate rising glucose, and lights flashing from right to left or top to bottom may indicate falling glucose. Other examples include lights that change size, brightness, and or contrast.

In some embodiments, the display 304 may comprise a light bar, where a percentage of the bar that is illuminated and/or the color of the light may represent the user's glucose level and/or a degree of risk associated with the indicated level. For example, the percentage of the bar that is illuminated may indicate the user's glucose level, while the color of the light bar may indicate the degree of risk associated with the indicated level. A color coded legend may be provided adjacent the light bar to help the viewer interpret the risk level associated with each color. In another example, a colored dot may be shown with a line extending from it, where the color represents risk and the line represents glucose level or range.

Lights may be used in various combinations to indicate any of the above conditions. For example, a blink pattern can be used with one LED. The blink pattern can be used to signify different information. Color 1 (such as blue) LED with one blink may be trending low, while Color 1 with two blinks may be hypoglycemic. Color 2 (such as yellow) LED with one blink may be trending high, while Color 2 with two blinks may be hyperglycemic. Other colors may be used to show different system alarms and/or calibration alerts. In another example, a single component LED may display up to three colors. Thus, with one LED and one light pipe, three different colors can be displayed with multiple patterns for each.

In another example, displayed patterns can follow patterns of a "mood ring," e.g. rather than discrete zones (high, target, low), as the user is approaching a different zone, the colors gradually shift. For example, red may indicate high, with shifts to dark pink then mid-pink then light pink as the user enters the target zone. The color may then gradually shift from light pink to white as the user enters the low zone.

In some embodiments, the output to the display 304 may provide positive feedback when the user is performing well, such as when the user stays within a desired glucose range for a set period of time. For example, the display 304 may show a calming or pleasing image such as a tree, a flower, etc., and as the user continues to perform well the image may continue to grow, or may transition from sickly looking to healthy looking. By contrast, if the user is not performing well, the display may provide negative feedback, such as causing the image to shrink, or look sickly, etc. These type of outputs provide cumulative information and/or progress toward a goal, and may be accompanied by additional information, such as a numerical indication of how many days have passed without a high glucose event and/or a low glucose event, a numerical indication of how many high glucose events or low glucose events have occurred within the past few days, weeks, etc., an amount of time spent within a desired range, etc.

The display 304 may include a sleep feature, in which the display 304 automatically dims or darkens after a set interval, and only "wakes up" in response to a user input and/or an alert condition. For example, the wearable device 21 and/or display 304 may include a touch sensor or a button (not shown). Touching the sensor or depressing the button wakes up the display 304 so that the user can view his or her current glucose condition. Such embodiments enhance the discreetness of the wearable device 21 and may also help to conserve battery power.

The wearable device 21 may further comprise a speaker for emitting one or more audible alerts. Such alerts may take the form of beeps, or of spoken words, such as "Your glucose is below the acceptable threshold. Please take action." Such alerts may be used in isolation and/or to supplement any visual information provided by the display 304, such as a loud beep when a high or low glucose condition occurs. The volume of the alerts may increase over time until the user takes action. Increasing volume is advantageous, because as glucose levels decrease, cognitive function also decreases. Thus, louder alarms may be more effective at lower glucose levels without increasing any annoyance to the user when glucose is at higher levels. In some embodiments, different visual patterns and/or audible tones may be used to signify different conditions. For example, a first pattern and/or a first tone may be provided for trending low, while a second pattern and/or a second tone may be provided for hypoglycemia, while a third pattern and/or a third tone may be provided for trending high, while a fourth pattern and/or a fourth tone may be provided for hyperglycemia, etc.

The wearable device 21 of FIG. 3 may further comprise a data storage module (not shown), such as flash memory or any other type of data storage. In such embodiments, the sensor electronics unit 12 may send data from the sensor 10 to the communication module 306 so that the data can be stored in the wearable device 21 storage. In such embodiments, the data need not be stored by the sensor electronics unit 12, so that the sensor electronics unit 12 may be simplified and made smaller and less expensive.

As discussed above, in some embodiments the communication module 306 may have both receive and transmit capabilities, such that the wearable device 21 may transmit information to one or more other devices. The wearable device 21 of FIG. 3 may thus act as a repeater that receives information from the sensor electronics unit 12 and forwards that information to another device or devices. In some embodiments, the repeater may store the data received from the sensor electronics unit 12 and relay the data to another device at regular intervals, or in response to a trigger, such as a user request. The repeater may forward the information in the same form in which it was received, and/or may process or partially process the received information before forwarding the processed or partially processed information. Either or both of the wearable device 21 and the other device may then provide an alert, if appropriate. The alert may take any form, such as one or more audible tones, and/or visual indicators.

The ability of the wearable device to repeat data from the sensor electronics unit 12 to another device also solves the problem of communication between different wireless protocols, such as between a manufacturer-specific medical device and a generic handheld consumer device (e.g., a mobile phone). Because handheld consumer devices use many different wireless technologies, the ability of the manufacturer-specific medical device to communicate with every available consumer device on the market is limited. As such, the wearable device may provide not only an alert interface, but also connectivity from the manufacturer-specific medical device to any of a wide variety of consumer devices. As one example, a manufacturer may provide a proprietary RF protocol from the sensor electronics unit to the wearable device, and the wearable device may be embedded with BLUETOOTH® technology for connectivity to certain mobile phones, enabling the sensor electronics unit to communicate with a consumer device that uses a wireless technology that is incompatible with the sensor electronics. The sensor electronics unit and the wearable device may be embedded with any combination of one or more, or two or more, of the following different communication protocols, respectively, including: radio frequency, infrared (IR), magnetic induction, BLUETOOTH®, BLUETOOTH® low energy (BLE), near-field communications (NFC), body area network (BAN), universal serial bus (USB), any of the wireless local area network (WLAN) communication standards, including the IEEE 802.11, 802.15, 802.16, 802.20, 802.22, and other 802 communication protocols, ZIGBEE®, wireless (e.g., cellular) telecommunication, paging network communication, magnetic induction, satellite data communication, general packet radio service (GPRS), the ANT protocol, and/or a proprietary communication protocol.

In embodiments in which data is forwarded from the wearable device 21 to another device upon user request, the request may be initiated using the wearable device 21 and/or the other device. For example, the wearable device 21 may include a button (not shown) or other input mechanism that the user activates or manipulates to initiate the data transfer from the wearable device 21 to the other device. Instead, or in addition, the other device may include a button or other input mechanism that the user activates or manipulates to initiate the data transfer from the wearable device 21 to the other device. The wearable device 21 may also include one or more buttons (not shown) for activating/silencing alarms/alerts and/or powering on/off the wearable device and/or connecting to the transmitter or receiver.

In any of the foregoing embodiments, the type of alert provided by the wearable device may be configurable. For example, the user may select one or more different types of alerts, such as audible alerts, visual alerts, and/or tactile alerts. Selections may be made using only the wearable device, and/or the wearable device may be connectable to a computing device and selections may be made using the computing device and then the selections stored on the wearable device through a wired or wireless connection. Various other settings may also be programmable, such as varying the intensity of alerts based on a time of day, or increasing the intensity of alerts when the user does not respond to a given alert within a set interval, where the duration of the interval may also be set by the user.

In any of the present embodiments, the sensor and/or sensor electronics may change color to reflect the user's current glucose level. For example, one color may be shown if the level is low, another color if the level is in a predefined range, and another color if the level is high. As the level increases or decreases, the intensity and/or brightness of the colors may also increase or decrease. The color could also blink or have different pulse patterns for other indications, such as for the breach of a low glucose limit.

Also in any of the present embodiments, the wearable device 21 may include additional functional components, such as a pedometer, a mechanism that detects movement, acceleration, orientation, etc., such as an accelerometer and/or a gyroscope, a start/stop exercise button, etc. The advantages of the foregoing components are explained in greater detail in U.S. patent application Ser. Nos. 13/801, 445, 13/802,424, 13/802,237, and 13/802,317, all filed on Mar. 3, 3013, the entire disclosures of which are hereby incorporated by reference herein and made a part of this disclosure.

The embodiments described above provide a wearable device that may be smaller and have limited functionality as compared to a typical receiver of a CGM system. The wearable device 21 can thus be worn discreetly to preserve the wearer's privacy regarding his or her health condition(s), and to save the user from embarrassment in certain social situations. Certain embodiments may also be water resistant, so that the wearable device can be worn during activities where a typical receiver would normally be set aside, such as water activities (swimming, bathing, etc.). Certain of the present embodiments may be used in place of a typical receiver, or as a supplement to a typical receiver.

The embodiments described above provide a further advantage in that they can be worn on the body, and thus can follow the user wherever he or she goes. As long as the user does not deliberately remove the wearable device, it will remain with him or her at all times, reducing the likelihood that the user will fail to receive an alert when his or her blood glucose is above or below a threshold value and/or trending high or low. Further, as long as the wearable device is being worn, it will always be in close proximity to the sensor electronics unit/transmitter. The transmitter can thus be tailored to be very small and to operate on very little power, because it need only communicate with the wearable device, which is always in close proximity. And with embodiments in which the wearable device is capable of storing data, the transmitter can send the data to the wearable device for storage so that the sensor electronics unit does not need to include any data storage, further enhancing the ability to reduce the size of the sensor electronics unit.

The present embodiments may also be integrated with an IFTTT ("IF This, Then That") protocol to provide the user with additional forms of alerts. For example, a user may program his or cellular phone with an IFTTT protocol that provides a phone call, e-mail, text message, etc. whenever the user does not respond to a given condition within a certain interval after a device provides an alert and/or provides glucose information. After the allotted interval has passed, the communication module then sends a notification to the user's IFTTT network, which then provides an additional alert through another device. For example, one such IFTTT protocol may be to provide the user with a phone call if he or she doesn't respond to a hypoglycemic alert within five minutes. In another example IFTTT protocol, in response to an alert, such as a hypoglycemic condition, the IFTTT protocol may unlock a door to the user's home, and provide an alert to a neighbor of the user that the user needs help. The user can thus be reassured that potentially dangerous conditions will be caught, even when the user is asleep or otherwise incapable or responding to alerts/alarms.

The present embodiments may also be capable of communicating with one or more other medical devices that are on or within the user. For example, some diabetics wear an insulin pump. When the wearable device receives a signal from the sensor electronics unit 12 that indicates the user's blood glucose is rising, the wearable device may send a signal to the insulin pump to administer an appropriate quantity of insulin to the user and/or alert the user of changes to the insulin pump administration (e.g., in a semi-closed loop or closed-loop configuration).

The present embodiments may include one or more features that reduce the burden on the user. For example, the wearable device may include a microphone and circuitry to enable voice recognition so that the user can issue commands to the system easily by speaking into the microphone, e.g., to request display of a current glucose concentration value. Such features that make using the system easier increase the likelihood of patient compliance. In another example, the system may display information when it detects movement, such as in the user's hand and/or wrist, which may indicate that the user is looking at the system. Certain gestures may be used to activate and/or inactivate the alert interface, including waking up the display and/or acknowledging an alert.

In certain embodiments, the repeater electronics could be snapped into a wearable device or a keychain, for example. This would allow the user to choose how they wanted to use the repeater at different times and/or so that the wearable device could be generic, while the repeater electronics could be exchanged depending on the type of wireless protocol used (e.g., depending on whether the user needs to transmit to a Galaxy phone (ANT+) or an iPhone (BLE)).

The embodiments described herein with reference to the wearable device 21 may provide one, some or all of the following advantages: because the device 21 is wearable, the display 304 is easily visible without a need to touch the wearable device 21 with either hand (also eliminates any need to locate the device, such as by digging through pockets or a purse); only the user may be aware of any alerts provided by the wearable device 21, so that the user is not embarrassed by alerts in social situations; enables the wearer to discreetly acknowledge the receipt of new information or an alert, so that additional information/alerts can be provided if no acknowledgement is received; the wearable device 21 may detect when the user is asleep and make appropriate adjustments to basal thresholds and/or rates based on the detected condition rather than making assumptions based on the time of day; the wearable device 21 may detect when the user is asleep and automatically make adjustments to the alert notifications, such as the volume or intensity thereof, to increase the likelihood that the user will wake up in response to an alert; and where data is forwarded from the wearable device 21 to another device, such as a smartphone 18, the user can discreetly review the data in private at any convenient time.

Some CGM systems include multiple devices for displaying sensor data. For example, referring to FIG. 1, a CGM system 100 may include a dedicated handheld receiver 16 (FIG. 2) with a display. But the user of such a system may also own a smartphone 18 that executes a CGM application. And, the user may also have one or more wearable devices 21 that can receive sensor data. When multiple devices are configured to receive information from the sensor system 8, the user may be confused as to which device is connected to the sensor system 8 at any given time. The user may thus not know whether the device that he or she is looking at has the most current sensor data available. The user may also be unsure as to which device he or she should use to acknowledge an alert sent by the sensor system 8.

Embodiments can solve these problems by designating one device in the CGM system to serve as a primary device, or hub, for receiving sensor data. In some embodiments, the smartphone 18 is the hub that controls the flow of data and/or alerts to other devices in the CGM system. In example implementations, the smartphone 18 is the only device in the CGM system that receives signals directly from the sensor system 8. The smartphone 18 may then forward the received data and/or alerts to other devices in the CGM system.

As discussed above, it may not always be convenient for a user to navigate through multiple screens to see current sensor data. As also discussed above, a user may not hear an alert if, for example, his or her smartphone 18 is buried deep within his or her briefcase, purse etc., or if the smartphone 18 is in silent mode because the user is in a movie theater, for example.

To solve these and other problems, the present embodiments may send sensor data and/or alerts to a hierarchy of devices in a designated order. For example, an alert (or non-alert sensor data) may be sent to a first device, such as the wearable device 21, that is readily viewable by the user. If the user acknowledges the alert on the first device within a designated interval, then no further action is taken. However, if the user does not acknowledge the alert on the first device within the designated interval, another alert may then be sent to a second device, such as the smartphone 18. If the user acknowledges the alert on the second device within a designated interval, then no further action is taken. However, if the user does not acknowledge the alert on the second device within the designated interval, another alert may then be sent to a third device, such as the key fob 14. This process may continue through any number of successive devices in the hierarchy. One or more alerts may also be sent, at any point in the process, to one or more other people, such as others in the user's social network, others who are nearby based on geolocation, etc. The hierarchy of devices and/or people that receive information and/or alerts in these embodiments may be preset or customized. Devices that receive information and/or alerts in these embodiments may establish communication with the user's CGM system based on proximity or other criteria.

The various tasks performed in connection with processes described above may be performed by a processor executing instructions embodied in a non-transitory computer-readable medium. For example, tasks may be performed by hardware, software, firmware, or any combination thereof, incorporated into one or more computing devices, such as one or more of the devices and/or systems described herein. It should be appreciated that the processes described herein may include any number of additional or alternative tasks. Further, any tasks described herein need not be performed in the illustrated/listed order, and the processes described herein may be incorporated into a more comprehensive procedure or process having additional functionality not described in detail herein.

Figure 6:
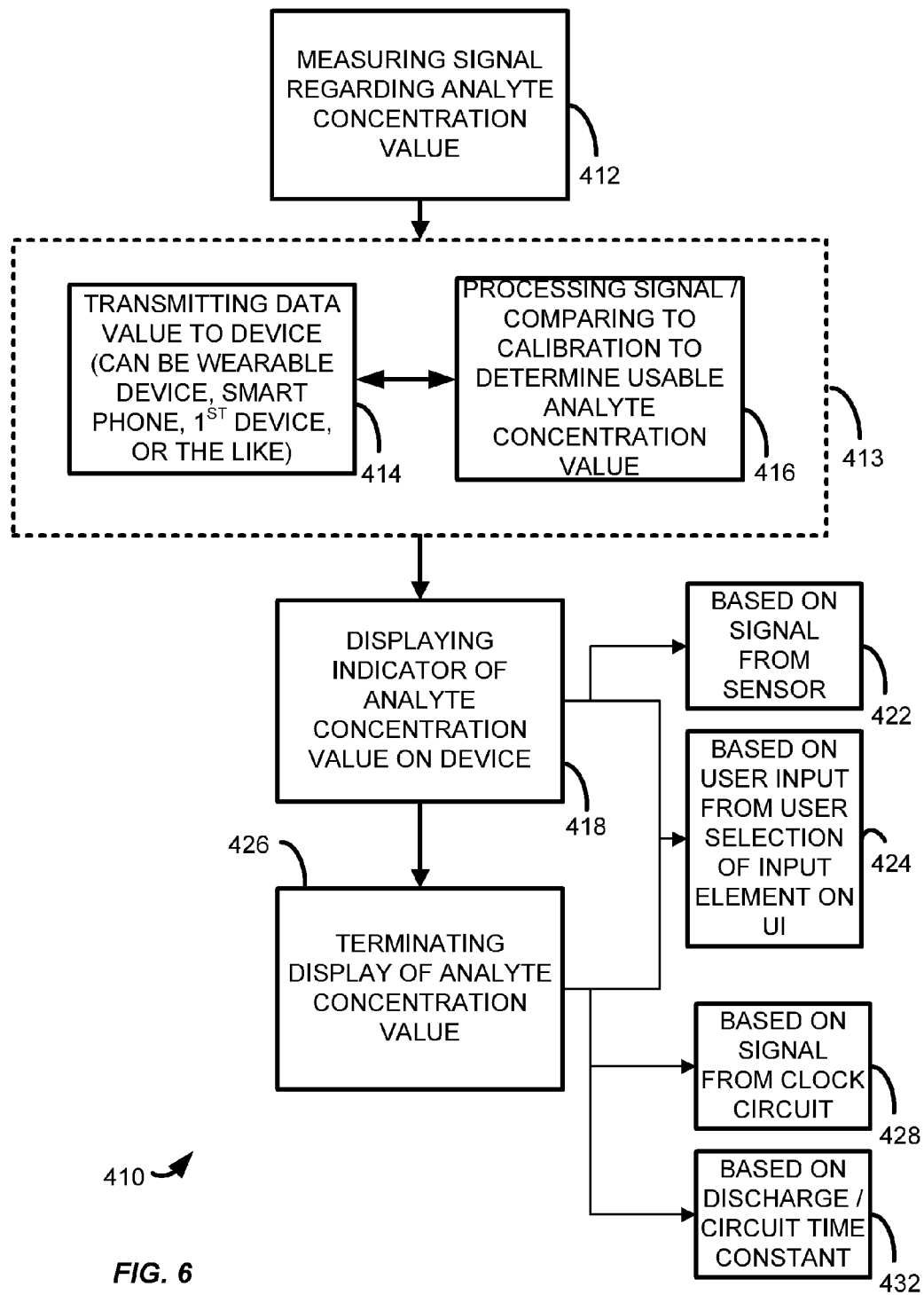

For example, referring to FIG. 6, a more detailed flowchart 410 is indicated in which physiological parameters such as analyte concentration values may be effectively conveyed to a user, e.g., a host. In a first step, an analyte concentration value is measured (step 412). A group of steps 413 may then be performed, including a step of potentially processing the measured signal and comparing the same to a calibration in order to determine a usable analyte concentration value which in turn may be displayed to a user (step 416). The processing step may be to smooth the data signal, and/or to perform other algorithmic steps to make the data signal appropriate for display and convenient for user. The comparing the signal to a calibration may be performed to determine what value the displayed signal should be, given prior measured calibration values.

Another step within the group of steps 413 is to transmit the data value to a device (step 414). The transmitting step 414 is generally performed by the sensor electronics. The group of steps 413 is grouped as the same may be performed in any order. For example, the sensor electronics may perform steps of processing and comparing to calibration values, and may then transmit the calibrated processed data value to a device for display. Alternatively, the sensor electronics may simply be a pass-through for the measured signal value, in which case the recipient of the measured signal value, e.g., the device to which the data is transmitted, may perform the signal processing and determination of a usable analyte value. It is also noted that the transmission of the data may include a step of appropriately formatting the transmitted data into a form required for reception and use of the data by a device. The processing and comparing to calibration steps may also be performed in such a way that, rather than a unique performance of each step by one or the other device, the steps may also be performed jointly by the combined devices, such that one device performs one portion of an algorithm and the other performs another portion.

In any case, having received the transmitted data value, an indicator of the data value, i.e., an indicator of the analyte concentration value, may be displayed on the device (step 418). In so doing, the received data may be appropriately formatted according to the display characteristics of the device. It is further noted in this regard that the wearable device 21, being particularly suited for display of such data values, may provide significant advantages over displaying data values on other devices. Certain advantages are described above, but it is also noted that by displaying the analyte concentration values on the wearable device, computational steps relating to display are removed from having to be performed by an underlying "hub" device such as a smart phone, thus rendering the same more efficient and generally allowing computational steps to be performed by those devices best suited for such steps. In essence, making both computing devices operate better.

Returning to the flowchart 410, the displayed indicator of an analyte concentration value may be based on one or more types of data from one or more physical devices. For example, in many cases the displayed indicator will be based on a signal or data from a physical sensor (step 422). As another example, the displayed indicator may be based on user input from user selection of an input element on a user interface (step 422), e.g., of a smart phone or of the wearable device 21, e.g., via a touchscreen. Put another way, data may be received at an I/O port (wired or wireless) of the device providing the indication, where the data is sourced from a wired or wireless port on a sensor electronics circuit or from a user interface I/O element.

The display may then be terminated of the analyte concentration value (step 426). In other words, the physical user interface is caused to transition from one mode of operation, displaying the indicator of the analyte concentration value (or other measured physiological parameter), to another mode of operation, in which the indicator is no longer displayed. Causes of the transition are described above, e.g., a received acknowledgment signal from a user on a physical user interface such as a touchscreen, expiration of a predetermined or preset (including user configurable) duration of time, a determination that the data is stale, or the like. In many of these algorithms, data is used (step 428) from a clock circuit, e.g., a timer chip. In other cases, the terminating may be based on data inherent in the circuit, e.g., an RC time constant, discharge time of a circuit element, and so on. And as noted user input (step 424) may also bear on the terminating step (step 426). For example, user activation of elements on the user interface may cause the display of data to be extended or termination of the display to occur more rapidly.

Figure 7:
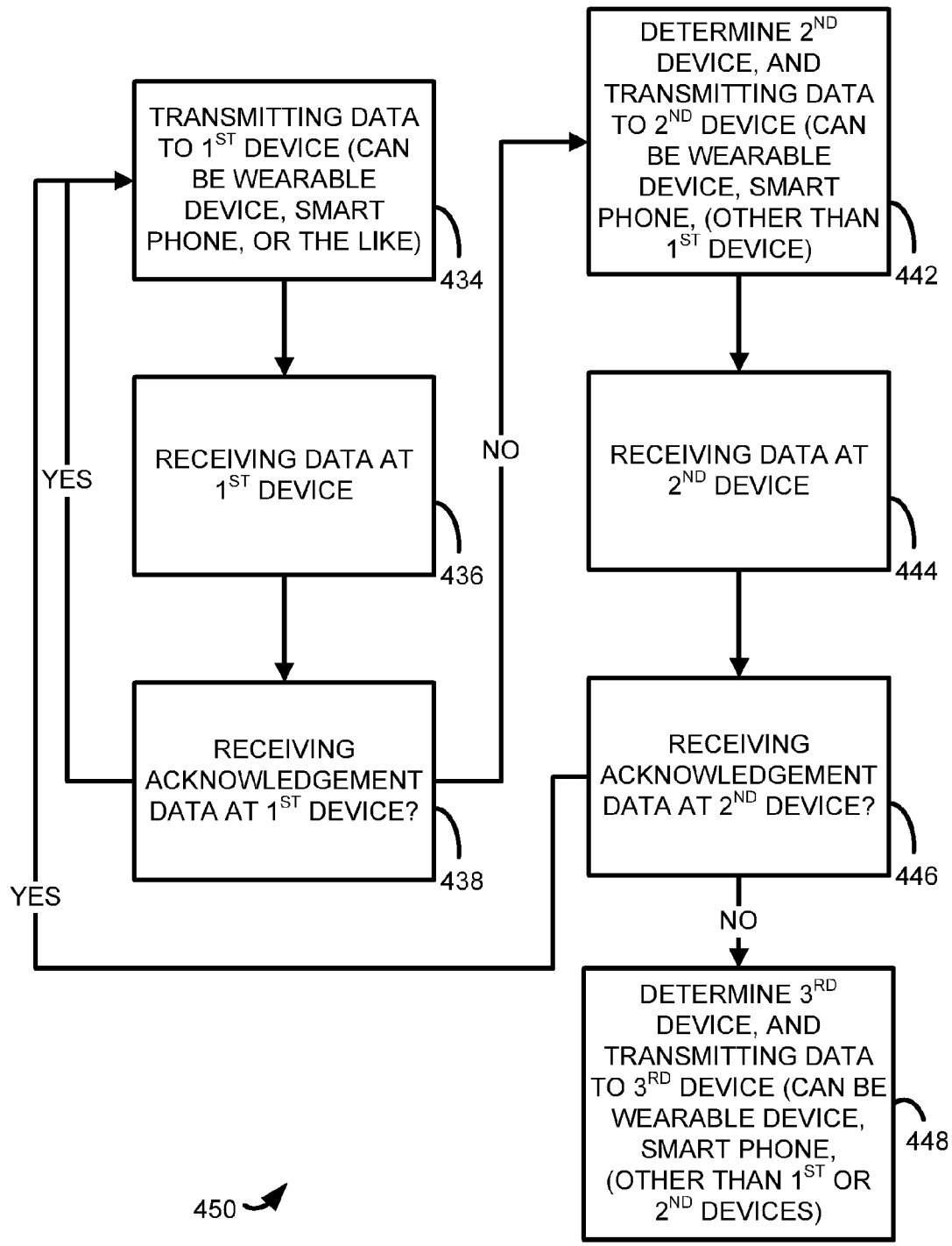

FIG. 7 is a flowchart 450 illustrating another more detailed method according to certain implementations of present principles. In a first step, data is transmitted to a first device for display (step 434). The data is typically from sensor electronics as described above, although other data sources are contemplated and encompassed by the scope of present principles. The data is typically received at an I/O port of the first device (step 436), and may constitute pushed or pulled data, in manners described elsewhere. The displayed data may invite acknowledgment by a user (step 438), and if indeed acknowledgment is received, the flow may proceed to the next data transmission (step 434). Such acknowledgment may be provided in a number of ways as described elsewhere herein, but generally involves data responsive to the displayed data being received at the first device, e.g., user activation of an activatable element on a touchscreen, or some other "analog" response to the display, including accelerometer or other motion-sourced data indicating that a user has viewed the display. For example, in some cases, a quick shake of the wrist may provide the acknowledgment.

If such an acknowledgment is not received, then this step may be performed of determining a second device to which the data should be transmitted for display, and transmitting the same to the second device (step 442). Data may then be received at the second device (step 444). A step similar to step 438 may then be performed, of determining a user acknowledgment of the data transmitted to the second device (step 446). If an acknowledgment is received, then flow may pass to the first step as before, e.g., upon the next time data is to be transmitted for display to a device, the same may be sent to the first device (step 434). However, in an alternate implementation, the transmitting device (which may be sensor electronics, a smart phone as hub, or the like) may also determine that a new operating mode should be entered, different from the first operating mode, in which a different device is chosen as the first device. In this case, upon the next occurrence of data to be transmitted, the same may be transmitted to the "new" first device. For example, perhaps a wristband wearable device is low on battery power, and thus no acknowledgment was received; in this case, a new wearable device, e.g., a Bluetooth® headset, may become in the new mode the first recipient of data, i.e., the "new" first device.

Returning to the flowchart 450, if no acknowledgment is received of the data at the second device (step 446), then a third device may be determined, and the data transmitted to the third device for display (step 448) and acknowledgment.

Various benefits inure to systems and methods according to present principles as described above. For example, by selecting one device for transmission, followed by a subsequent device if no acknowledgment is received, a significant benefit is realized, e.g., power savings, and well as significantly-reduced device computing load, as only one device (potentially) has to receive data at a time. Additional devices need only be caused to receive data if there is no acknowledgment from the first device. Transmissions of data need not be formatted for multiple devices, e.g., with potentially multiple data and transmission protocols. Data routing to different devices, according to the occurrence of one or more data conditions, e.g., user acknowledgments as determined by data received from a user interface, may occur at the same time as other physiological data is being measured by the sensor and potentially transmitted to the various devices. In other words, while data routing is occurring, other subsequent data may be measured and processed, analyzed, or like steps may be performed. Yet another benefit is that the potential use of the multiple devices in the flowchart of FIG. 7 also means that data from the different and varied sensors (as may be provided from the multiple devices) may be transmitted to the "hub" device, e.g., a smart phone, to monitor multiple physiological parameters and employ the same in monitoring patient health.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

In some embodiments, the system may execute various applications, for example, a CGM application, which may be downloaded to the receiver or other electronic device over the Internet and/or a cellular network, and the like. Data for various applications may be shared between the device and one or more other devices/systems, and stored by cloud or network storage and/or on one or more other devices/systems. The data so stored may form the basis of the dynamic reports described above.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIGS. 1-3) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

The system and method may be fully implemented in any number of computing devices, as described above in connection with device 200 of FIG. 2. Typically, instructions are laid out on computer readable media, generally non-transitory, and these instructions are sufficient to allow a processor in the computing device to implement the method of the embodiments, particularly as detailed in the flowcharts shown in FIGS. 4-7. The computer readable medium may be a hard drive or solid state storage having instructions that, when run, are loaded into random access memory. Inputs to the application, e.g., from one or more sensors or one or more users, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Given this teaching, any number of other tangible outputs will also be understood to be contemplated by the embodiments. For example, outputs may be stored on a memory chip, hard drive, flash drives, flash memory, optical media, magnetic media, or any other type of output. It should also be noted that the embodiments may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or WiFi—connected device downloads a copy of the application to their device from a server using a wireless internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the above system where analyte concentration display and review are contemplated, the plural inputs may allow plural users to input relevant data and control the display and review at the same time.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

The above description presents various embodiments of the present invention, and the manner and process of making and using them, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A wearable device for providing information to a user regarding the user's blood glucose value, the device comprising:
    a communication module having an input/output port for receiving data transmitted from a continuous glucose monitoring system including a sensor, a signal from the sensor transformed into the data for transmission, wherein the communication module is configured to receive a first dataset and a second dataset:
    a display configured to display a first information based on the first dataset for a set duration; and
    an input module for enabling the user to acknowledge that the first information has been viewed,
    wherein when the user acknowledges that the first information has been viewed, the communication module sends an acknowledgement signal to the glucose monitoring system,
    wherein the display is configured to cease displaying the first information after the continuous glucose monitoring system receives the acknowledgement signal from the communication module, and
    wherein, after the set duration elapses, the display is configured to no longer display the first information until the communication module receives the second dataset from the glucose monitoring system.

2. The device of claim 1, wherein the signal is received from a computing device of the continuous glucose monitoring system.

3. The device of claim 1, wherein the computing device is a smartphone.

4. The device of claim 1, wherein the first information displayed includes at least one of a glucose value, a glucose trend, an alert, and a time when the signal was received from the continuous glucose monitoring system.

5. The device of claim 1, wherein the device further comprises a timer chip, timer circuit, or timer implemented by program instructions on a non-transitory computer-readable medium.

6. The device of claim 5, wherein the timer measures the set duration.

7. The device of claim 1, wherein the set duration begins when the data is received from the continuous glucose monitoring system.

8. The device of claim 1, wherein the display of the first information commences without any user interaction.

9. The device of claim 1, wherein a brightness of the displayed first information fades as the set duration elapses.

10. The device of claim 1, wherein the set duration is in the range of one second to twenty minutes.

11. The device of claim 1, wherein the display comprises one or more of electronic paper, electronic ink, an electrophoretic display, a gyricon, a liquid crystal display, one or more light-emitting diodes, one or more organic light-emitting diodes, a color-changing material, a pattern-changing material, magnetic materials, piezo-electric materials, vibration patterns, heat/cold patterns, one or more light pipes with single-color or multicolor light-emitting diodes or organic light-emitting diodes, a transparent and flexible multi-touch surface, or an interactive glass surface.

12. The device of claim 1, further comprising a band configured to be worn about a wrist of a wearer, wherein the communication module and the display are incorporated into the band.

13. The device of claim 1, wherein the display is further configured to display a status flag that indicates when the device last received the signal from the continuous glucose monitoring system.

* * * * *

UNITED STATES PATENT AND TRADEMARK OFFICE
CERTIFICATE OF CORRECTION

PATENT NO. : 10,004,435 B2
APPLICATION NO. : 14/538701
DATED : June 26, 2018
INVENTOR(S) : Shawn Larvenz et al.

It is certified that error appears in the above-identified patent and that said Letters Patent is hereby corrected as shown below:

In Column 7 at Line 25, Change "andrenostenedione;" to --androstenedione;--.

In Column 7 at Line 40, Change "diptheria/" to --diphtheria/--.

In Column 7 at Line 47, Change "perioxidase;" to --peroxidase;--.

In Column 7 at Line 56, Change "sissomicin;" to --sisomicin;--.

In Column 7 at Line 60-61, Change "duodenalisa," to --duodenalis,--.

In Column 8 at Line 1, Change "Trepenoma pallidium," to --Treponema pallidum,--.

In Column 8 at Line 2, Change "stomatis" to --stomatitis--.

In Column 8 at Line 23, Change "(barbituates," to --(barbiturates,--.

In Column 18 at Line 16, Change "and or" to --and/or--.

In Column 31 at Line 55, In Claim 1, change "dataset:" to --dataset;--.

Signed and Sealed this
Twenty-fifth Day of September, 2018

Andrei Iancu
*Director of the United States Patent and Trademark Office*